United States Patent [19]

O'Rand et al.

[11] Patent Number: 5,480,799
[45] Date of Patent: Jan. 2, 1996

[54] SPERM ANTIGEN CORRESPONDING TO A SPERM ZONA BINDING PROTEIN AUTOANTIGENIC EPITOPE

[75] Inventors: Michael G. O'Rand; Esther E. Widgren; Richard T. Richardson; Isabel A. Lea, all of Chapel Hill, N.C.

[73] Assignee: The University of North Carolina at Chapel Hill, Chapel Hill, N.C.

[21] Appl. No.: 166,195

[22] Filed: Dec. 10, 1993

[51] Int. Cl.$^6$ .............................. C12N 1/21; C12N 15/12; C12N 1/19; C12N 5/10

[52] U.S. Cl. .................. 435/252.3; 435/69.1; 435/172.3; 435/320.1; 435/240.2; 435/254.2; 435/254.21; 536/23.1; 536/23.5; 536/25.3; 424/93.2; 424/200.1

[58] Field of Search .................................. 435/69.1, 71.1, 435/172.3, 252.3, 240.2, 320.1, 254.2, 254.21; 424/93.2, 184.1, 192.1, 197.11, 200.1, 811; 536/23.1, 23.5, 25.3

[56] References Cited

U.S. PATENT DOCUMENTS 5,175,148   12/1992   O'Rand et al. .

FOREIGN PATENT DOCUMENTS

WO92/09684   6/1992   WIPO .

OTHER PUBLICATIONS

R. T. Richardson and M. G. O'Rand; *Cloning and Sequencing of the Rabbit Sperm Zona Binding Protein, RSA–3; Mol. Biol. Cell* 3, 15a (1992).

R. B. Shabanowitz and M. G. O'Rand; *Molecular Changes in the Human Zona Pellucida Associated with Fertilization and Human Sperm–Zona Interactions; Ann. N.Y. Acad. Sci.* 541, pp. 621–632 (1988).

*Primary Examiner*—Mary E. Mosher
*Assistant Examiner*—Laurie Scheiner
*Attorney, Agent, or Firm*—Bell, Seltzer, Park & Gibson

[57] ABSTRACT

The present invention involves DNA encoding a mammalian Sp 17 protein, particularly human Sp17 protein, or antigenic peptides which are fragments thereof, along with said antigenic fragments. These proteins and peptides are useful as immunocontraceptive agents and/or for the diagnosis of autoimmune infertility. Avirulent host cells which express the antigeenic proteins or peptides and which are useful as immunocontraceptive agents are also disclosed.

5 Claims, 7 Drawing Sheets

FIG. 7

|  | 4 | 28 | 34 | 49 | 55 | 61 |
|---|---|---|---|---|---|---|
| RABSP17 | MSI PFSNTHYRIPQGFGNLLEGLTREIL | REQPD | NIPAFAAAYFENLLEK | REKTN | FDPAEWGAKVD |
| MUSSP17 | MSI PFSNTHYRIPQGFGNLLEGLTREIL | REQPD | NIPAFAAAYFENLLEK | REKTS | FDPAEWGAKVE |
| HUMSP17 | MSI PFSNTHYRIPQGFGNLLEGLTREIL | REQPD | NIPAFAAAYFESLLEK | REKTN | FDPAEWGSKVE |

|  | 82 | | 117 |
|---|---|---|---|
| RABSP17 | DRFYNNHAFQEHESEKC | EA--EEKSQSVT-EEEETPVLTI--DSEDDKDKEE | MAALKIQAAFRGH |
| MUSSP17 | DRFYNNHAFKEQEQVEK | CE-QELAKSSG-REETPVTPFEESTEEEREQEE | AAALKIQSLFRGH |
| HUMSP17 | DRFYNNHAFEEQEPPEK | SDpkQEESQISGkEEETSV-TILDSSEEDKEKEE | VAAVKIQAAFRGH |

|  | 137 | 151 |
|---|---|---|
| RABSP17 | AREDVKKI | RTNKAEEETEENN- |
| MUSSP17 | AREEVKKM | KSDKNENLKEEADn |
| HUMSP17 | AREEAKKM | KTNSLQNEEKEENk |

5,480,799

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
  ( A ) LENGTH: 854 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: CDS
  ( B ) LOCATION: 32..487

( x i ) SEQUENCE DESCRIPTION: SEQ ID NO:1:

```
GGAGGTTCCA TAGGCAGTTC TTACCAAGAA G ATG TCG ATT CCA TTC TCC AAC                 52
                                  Met Ser Ile Pro Phe Ser Asn
                                   1                5

ACC CAC TAC CGA ATT CCA CAA GGA TTT GGG AAT CTT CTT GAA GGG CTG              100
Thr His Tyr Arg Ile Pro Gln Gly Phe Gly Asn Leu Leu Glu Gly Leu
         10                  15                  20

ACA CGC GAG ATT CTG AGA GAG CAA CCG GAC AAT ATA CCA GCT TTT GCA              148
Thr Arg Glu Ile Leu Arg Glu Gln Pro Asp Asn Ile Pro Ala Phe Ala
     25                  30                  35

GCA GCC TAT TTT GAG AGC CTT CTA GAG AAA AGA GAG AAA ACC AAC TTT              196
Ala Ala Tyr Phe Glu Ser Leu Leu Glu Lys Arg Glu Lys Thr Asn Phe
 40                  45                  50                  55

GAT CCA GCA GAA TGG GGG AGT AAG GTA GAA GAC CGC TTC TAT AAC AAT              244
Asp Pro Ala Glu Trp Gly Ser Lys Val Glu Asp Arg Phe Tyr Asn Asn
                 60                  65                  70

CAT GCA TTC GAG GAG CAA GAA CCA CCT GAG AAA AGT GAT CCT AAA CAA              292
His Ala Phe Glu Glu Gln Glu Pro Pro Glu Lys Ser Asp Pro Lys Gln
             75                  80                  85

GAA GAG TCT CAG ATA TCT GGG AAG GAG GAA GAG ACA TCA GTC ACC ATC              340
```

```
              Glu  Glu  Ser  Gln  Ile  Ser  Gly  Lys  Glu  Glu  Glu  Thr  Ser  Val  Thr  Ile
                        90                       95                      100

TTA  GAC  TCT  TCT  GAG  GAA  GAT  AAG  GAA  AAA  GAA  GAG  GTT  GCT  GCT  GTC                388
Leu  Asp  Ser  Ser  Glu  Glu  Asp  Lys  Glu  Lys  Glu  Glu  Val  Ala  Ala  Val
          105                      110                     115

AAA  ATC  CAA  GCT  GCC  TTC  CGG  GGA  CAC  ATA  GCC  AGA  GAG  GAG  GCA  AAG                436
Lys  Ile  Gln  Ala  Ala  Phe  Arg  Gly  His  Ile  Ala  Arg  Glu  Glu  Ala  Lys
120                           125                     130                          135

AAA  ATG  AAA  ACA  AAT  AGT  CTT  CAA  AAT  GAG  GAA  AAA  GAG  GAA  AAC  AAG                484
Lys  Met  Lys  Thr  Asn  Ser  Leu  Gln  Asn  Glu  Glu  Lys  Glu  Glu  Asn  Lys
                    140                      145                     150

TGAGGACACT  GGTTTTACCT  CCAGGAAACA  TGAAAAATAA  TCCAAATCCA  TCCATCAACC                          544

TTCTTATTAA  TGTCATTTCT  CCTTGAGGAA  GGAAGATTTG  ATGTTGTGAA  ATAACATTCG                          604

TTACTGTTGT  GAAAATCTGT  CATGAGCATT  TGTTTAATAA  GCATACCATT  GAAACATGCC                          664

ACTTGAAGAT  TTCTCTGAGA  TCATGAGTTT  GTTTACACTT  GTCTCAAGCC  TATCTATAGA                          724

GACCCTTGGA  TTTAGAATTA  TAGAACTAAA  GTATCTGAGA  TTACAGAGAT  CTCAGAGGTT                          784

ATGTGTTCTA  ACTATTATCA  AATGAATAAA  TCCTCTCTAT  CACATCCCCC  AAAAAAAAAA                          844

AAAAAAAAAA                                                                                     854
```

( 2 ) INFORMATION FOR SEQ ID NO:2:

( i ) SEQUENCE CHARACTERISTICS:
        ( A ) LENGTH: 151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Ile  Pro  Phe  Ser  Asn  Thr  His  Tyr  Arg  Ile  Pro  Gln  Gly  Phe
 1                  5                        10                      15

Gly  Asn  Leu  Leu  Glu  Gly  Leu  Thr  Arg  Glu  Ile  Leu  Arg  Glu  Gln  Pro
               20                       25                      30

Asp  Asn  Ile  Pro  Ala  Phe  Ala  Ala  Ala  Tyr  Phe  Glu  Ser  Leu  Leu  Glu
          35                       40                      45

Lys  Arg  Glu  Lys  Thr  Asn  Phe  Asp  Pro  Ala  Glu  Trp  Gly  Ser  Lys  Val
     50                       55                      60

Glu  Asp  Arg  Phe  Tyr  Asn  Asn  His  Ala  Phe  Glu  Glu  Gln  Glu  Pro  Pro
65                       70                      75                           80

Glu  Lys  Ser  Asp  Pro  Lys  Gln  Glu  Glu  Ser  Gln  Ile  Ser  Gly  Lys  Glu
                    85                       90                      95

Glu  Glu  Thr  Ser  Val  Thr  Ile  Leu  Asp  Ser  Ser  Glu  Glu  Asp  Lys  Glu
               100                     105                     110

Lys  Glu  Glu  Val  Ala  Ala  Val  Lys  Ile  Gln  Ala  Ala  Phe  Arg  Gly  His
          115                     120                     125

Ile  Ala  Arg  Glu  Glu  Ala  Lys  Lys  Met  Lys  Thr  Asn  Ser  Leu  Gln  Asn
     130                     135                     140

Glu  Glu  Lys  Glu  Glu  Asn  Lys
145                     150
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear 5,480,799

19

-continued ( i i ) MOLECULE TYPE: peptide ( i i i ) HYPOTHETICAL: NO ( x i ) SEQUENCE DESCRIPTION: SEQ ID NO:3:

```
Met  Ser  Ile  Pro  Phe  Ser  Asn  Thr  His  Tyr
1                   5                        10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

```
Pro  Phe  Ser  Asn  Thr  His  Tyr  Arg  Ile  Pro
1                   5                        10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

```
Asn  Thr  His  Tyr  Arg  Ile  Pro  Gln  Gly  Phe
1                   5                        10
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

```
Tyr  Arg  Ile  Pro  Gln  Gly  Phe  Gly  Asn  Leu
1                   5                        10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:7:

```
    Pro  Gln  Gly  Phe  Gly  Asn  Leu  Leu  Glu  Gly
    1              5                        10
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
    Phe  Gly  Asn  Leu  Leu  Glu  Gly  Leu  Thr  Arg
    1              5                        10
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
    Leu  Leu  Glu  Gly  Leu  Thr  Arg  Glu  Ile  Leu
    1              5                        10
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
    Gly  Leu  Thr  Arg  Glu  Ile  Leu  Arg  Glu  Gln
    1              5                        10
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
    Arg  Glu  Ile  Leu  Arg  Glu  Gln  Pro  Asp  Asn
    1              5                        10
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
    Leu  Arg  Glu  Gln  Pro  Asp  Asn  Ile  Pro  Ala
    1              5                        10
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
    Gln  Pro  Asp  Asn  Ile  Pro  Ala  Phe  Ala  Ala
    1              5                        10
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
    Asn  Ile  Pro  Ala  Phe  Ala  Ala  Ala  Tyr  Phe
    1              5                        10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
    Ala  Phe  Ala  Ala  Ala  Tyr  Phe  Glu  Asn  Leu
    1              5                        10
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
    Ala  Ala  Tyr  Phe  Glu  Asn  Leu  Leu  Glu  Lys
    1              5                        10
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Phe Glu Asn Leu Leu Glu Lys Arg Glu Lys
1               5                   10

( 2 ) INFORMATION FOR SEQ ID NO:18:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:18:

Leu Leu Glu Lys Arg Glu Lys Thr Asn Phe
1               5                   10

( 2 ) INFORMATION FOR SEQ ID NO:19:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:19:

Lys Arg Glu Lys Thr Asn Phe Asp Pro Ala
1               5                   10

( 2 ) INFORMATION FOR SEQ ID NO:20:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:20:

Lys Thr Asn Phe Asp Pro Ala Glu Trp Gly
1               5                   10

( 2 ) INFORMATION FOR SEQ ID NO:21:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:21:

Phe Asp Pro Ala Glu Trp Gly Ala Lys Val
1               5                   10

( 2 ) INFORMATION FOR SEQ ID NO:22:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:22:

Ala Glu Trp Gly Ala Lys Val Asp Asp Arg
1               5                   10

( 2 ) INFORMATION FOR SEQ ID NO:23:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Gly Ala Lys Val Asp Asp Arg Phe Tyr Asn
1               5                   10

( 2 ) INFORMATION FOR SEQ ID NO:24:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Val Asp Asp Arg Phe Tyr Asn Asn His Ala
1               5                   10

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Arg Phe Tyr Asn Asn His Ala Phe Gln Glu
1               5                   10

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Asn Asn His Ala Phe Gln Glu His Glu Ser
1               5                   10

( 2 ) INFORMATION FOR SEQ ID NO:27:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Ala Phe Gln Glu His Glu Ser Glu Lys Cys
1               5                   10

( 2 ) INFORMATION FOR SEQ ID NO:28:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:28:

Glu His Glu Ser Glu Lys Cys Glu Ala Glu
1               5                   10

( 2 ) INFORMATION FOR SEQ ID NO:29:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:29:

Ser Glu Lys Cys Glu Ala Glu Glu Lys Ser
1               5                   10

( 2 ) INFORMATION FOR SEQ ID NO:30:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:30:

Cys Glu Ala Glu Glu Lys Ser Gln Ser Val
1               5                   10

( 2 ) INFORMATION FOR SEQ ID NO:31:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:31:

Glu Glu Lys Ser Gln Ser Val Thr Glu Glu
1               5                   10

( 2 ) INFORMATION FOR SEQ ID NO:32:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:32:

```
Ser Gln Ser Val Thr Glu Glu Thr Pro
1               5                   10
```

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Val Thr Glu Glu Glu Thr Pro Val Leu Thr
1               5                   10
```

( 2 ) INFORMATION FOR SEQ ID NO:34:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
Glu Glu Thr Pro Val Leu Thr Ile Asp Ser
1               5                   10
```

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

```
Pro Val Leu Thr Ile Asp Ser Glu Asp Asp
1               5                   10
```

( 2 ) INFORMATION FOR SEQ ID NO:36:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
Thr Ile Asp Ser Glu Asp Asp Lys Asp Lys
1               5                   10
```

( 2 ) INFORMATION FOR SEQ ID NO:37:

( i ) SEQUENCE CHARACTERISTICS:
        ( A ) LENGTH: 10 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:37:

```
Ser  Glu  Asp  Asp  Lys  Asp  Lys  Glu  Glu  Met
1                   5                        10
```

( 2 ) INFORMATION FOR SEQ ID NO:38:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Asp  Lys  Asp  Lys  Glu  Glu  Met  Ala  Ala  Leu
1                   5                        10
```

( 2 ) INFORMATION FOR SEQ ID NO:39:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Lys  Glu  Glu  Met  Ala  Ala  Leu  Lys  Ile  Gln
1                   5                        10
```

( 2 ) INFORMATION FOR SEQ ID NO:40:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Met  Ala  Ala  Leu  Lys  Ile  Gln  Ala  Ala  Phe
1                   5                        10
```

( 2 ) INFORMATION FOR SEQ ID NO:41:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Leu  Lys  Ile  Gln  Ala  Ala  Phe  Arg  Gly  His
1                   5                        10
```

( 2 ) INFORMATION FOR SEQ ID NO:42:

( i ) SEQUENCE CHARACTERISTICS:
        ( A ) LENGTH: 10 amino acids
        ( B ) TYPE: amino acid (C) STRANDEDNESS: single
                (D) TOPOLOGY: linear (ii) MOLECULE TYPE: peptide (xi) SEQUENCE DESCRIPTION: SEQ ID NO:42:

Gln  Ala  Ala  Phe  Arg  Gly  His  Leu  Ala  Arg
        1                   5                        10

(2) INFORMATION FOR SEQ ID NO:43:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:43:

Phe  Arg  Gly  His  Leu  Ala  Arg  Glu  Asp  Val
        1                   5                        10

(2) INFORMATION FOR SEQ ID NO:44:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:44:

His  Leu  Ala  Arg  Glu  Asp  Val  Lys  Lys  Ile
        1                   5                        10

(2) INFORMATION FOR SEQ ID NO:45:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:45:

Arg  Glu  Asp  Val  Lys  Lys  Ile  Arg  Thr  Asn
        1                   5                        10

(2) INFORMATION FOR SEQ ID NO:46:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:46:

Val  Lys  Lys  Ile  Arg  Thr  Asn  Lys  Ala  Glu
        1                   5                        10

(2) INFORMATION FOR SEQ ID NO:47:

(i) SEQUENCE CHARACTERISTICS:
                (A) LENGTH: 10 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:47:

Ile Arg Thr Asn Lys Ala Glu Glu Glu Thr
1               5                   10

(2) INFORMATION FOR SEQ ID NO:48:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:48:

Asn Lys Ala Glu Glu Glu Thr Glu Glu Asn
1               5                   10

(2) INFORMATION FOR SEQ ID NO:49:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:49:

Lys Ala Glu Glu Glu Thr Glu Glu Asn Asn
1               5                   10

(2) INFORMATION FOR SEQ ID NO:50:

(i) SEQUENCE CHARACTERISTICS:
(A) LENGTH: 145 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:50:

Met Ser Ile Pro Phe Ser Asn Thr His Tyr Arg Ile Pro Gln Gly Phe
1               5                   10                  15

Gly Asn Leu Leu Glu Gly Leu Thr Arg Glu Ile Leu Arg Glu Gln Pro
                20                  25                  30

Asp Asn Ile Pro Ala Phe Ala Ala Ala Tyr Phe Glu Asn Leu Leu Glu
                35                  40                  45

Lys Arg Glu Lys Thr Asn Phe Asp Pro Ala Glu Trp Gly Ala Lys Val
        50                  55                  60

Asp Asp Arg Phe Tyr Asn Asn His Ala Phe Gln Glu His Glu Ser Glu
65                  70                  75                  80

Lys Cys Glu Ala Glu Glu Lys Ser Gln Ser Val Thr Glu Glu Glu Thr
                85                  90                  95

Pro Val Leu Thr Ile Asp Ser Glu Asp Asp Lys Asp Lys Glu Glu Met
                100                 105                 110

Ala Ala Leu Lys Ile Gln Ala Ala Phe Arg Gly His Ala Arg Glu Asp
                115                 120                 125

```
            Val  Lys  Lys  Ile  Arg  Thr  Asn  Lys  Ala  Glu  Glu  Thr  Glu  Glu  Asn
                 130                 135                 140

Asn
            145
```

(2) INFORMATION FOR SEQ ID NO:51:

(i) SEQUENCE CHARACTERISTICS:
       (A) LENGTH: 148 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:51:

```
            Met  Ser  Ile  Pro  Phe  Ser  Asn  Thr  His  Tyr  Arg  Ile  Pro  Gln  Gly  Phe
            1              5                             10                       15

Gly  Asn  Leu  Leu  Glu  Gly  Leu  Thr  Arg  Glu  Ile  Leu  Arg  Glu  Gln  Pro
                           20                      25                       30

Asp  Asn  Ile  Pro  Ala  Phe  Ala  Ala  Ala  Tyr  Phe  Glu  Asn  Leu  Leu  Glu
                      35                      40                            45

Lys  Arg  Glu  Lys  Thr  Ser  Phe  Asp  Pro  Ala  Glu  Trp  Gly  Ala  Lys  Val
                 50                      55                       60

Glu  Asp  Arg  Phe  Tyr  Asn  Asn  His  Ala  Phe  Lys  Glu  Gln  Glu  Gln  Val
            65                      70                       75                           80

Glu  Lys  Cys  Glu  Gln  Glu  Leu  Ala  Lys  Ser  Ser  Gly  Arg  Glu  Glu  Thr
                                85                      90                            95

Pro  Val  Thr  Pro  Phe  Glu  Glu  Ser  Thr  Glu  Glu  Glu  Arg  Glu  Gln  Glu
                           100                     105                      110

Glu  Ala  Ala  Ala  Leu  Lys  Ile  Gln  Ser  Leu  Phe  Arg  Gly  His  Ala  Arg
                           115                     120                      125

Glu  Glu  Val  Lys  Lys  Met  Lys  Ser  Asp  Lys  Asn  Glu  Asn  Leu  Lys  Glu
                 130                     135                      140

Glu  Ala  Asp  Asn
            145
```

SPERM ANTIGEN CORRESPONDING TO A SPERM ZONA BINDING PROTEIN AUTOANTIGENIC EPITOPE

This invention was made with Government Support under Grant No. U54 HD29009 from the National Institutes of Health. The Government has certain rights to this invention.

FIELD OF THE INVENTION

The present invention relates to antigens which correspond to autoantigenic epitopes on a sperm zona pellucida binding protein, along with therapeutic and diagnostic methods employing the same.

BACKGROUND OF THE INVENTION

Autoantigens are tissue components of an organism to which that organism directs an immune response. The condition which results from such a self-directed immune response is known as autoimmunity (or "autoallergy"). Proteins on or on sperm are known to be potent autoantigens, and autoimmunity to such proteins is believed a significant cause of infertility.

R. Shabanowitz and M. O'Rand, Ann. N.Y. Acad. Sci. 541, 621–632 (1988), at FIG. 7, describes various human proteins which have affinity for human zona pellucida.

M. O'Rand and E. Widgren, U.S. Pat. No. 5,175,148, discloses a sperm antigen which corresponds to an autoantigenic epitope of Rabbit Sperm Membrane Autoantigen (RSA)- RSA is now known to be a family of four low molecular weigh glycoproteins (RSA-1,2,3,4: 14K, 16K, 17K, 18K) which function as high affinity zona binding proteins. The cloning of rabbit RSA 3 (also called "sp17") is described in R. Richardson and M. O'Rand, Mol. Biol. Cell. 3, 15a (1992).

SUMMARY OF THE INVENTION

A first aspect of the present invention is isolated DNA encoding a human Sp 17 protein or antigenic peptides which are fragments thereof selected from the group consisting of: (a) isolated DNA (e.g., the DNA of SEQ ID NO:1) which encodes the human Sp 17 protein having the amino acid sequence given herein as SEQ ID NO:2; (b) isolated DNA which hybridizes to isolated DNA of (a) above and which encodes a human Sp 17 protein; (c) isolated DNA differing from the isolated DNAs of (a) and (b) above in nucleotide sequence due to the degeneracy of the genetic code, and which encodes a human Sp 17 protein; and fragments of the foregoing which encode antigenic peptides (i.e., peptides which bind antibodies which bind to human Sp 17 protein, as described below, typically peptides of from 6 to twenty-five amino acids in length). These proteins and peptides are sometimes referred to as the "antigen" below, and are useful as immunocontraceptive agents and/or for the diagnosis of autoimmune infertility, as discussed below.

A second aspect of the present invention is a recombinant DNA sequence comprising vector DNA and a DNA as given above.

A third aspect of the present invention is a host cell containing a recombinant DNA sequence as given above and capable of expressing the encoded Sp 17 protein or antigenic peptide fragment thereof.

A fourth aspect of the present invention is antigenic peptides (these also being referred to as the "antigen" or "antigens" hereinbelow), useful as an immunocontraceptive agent or for the diagnosis of autoimmune infertility, selected from the group consisting of (1) antigenic fragments of mammalian Sp17 protein which are from six to twenty-five amino acids in length and (2) the antigenic equivalents thereof, said antigenic equivalents being: (a) a modified fragment comprising said antigenic fragment modified by the replacing of one or more amino acids to the sequence thereof; or (b) a longer peptide which incorporates the sequence of said antigenic fragment and which has (i) up to four extra amino acid residues attached to the C-terminal end of said sequence, (ii) up to four extra amino acid residues attached to the N-terminal end of said sequence, or (iii) up to four extra amino acid residues attached to the C-terminal end of said sequence and up to four extra amino acid residues attached to the N-terminal end of said sequence; wherein said antigenic equivalents bind to antibodies which to said antigenic fragments of mammalian Sp17 protein. The antigenic fragments of mammalian Sp17 protein are selected from the group consisting of (i) amino acid 4 to amino acid 28 fragments, (ii) amino acid 34 to amino acid 49 fragments, (iii) amino acid 55 to amino acid 82 fragments, (iv) amino acid 117 to amino acid 137 fragments, and (v) fragments of (i) through (iv) which are at least six amino acids in length.

A fifth aspect of the present invention is an immunocontraceptive method which comprises administering to a subject (e.g., a female subject) an antigen as described above in an amount effective to reduce the fertility of the subject.

A sixth aspect of the present invention is an immunocontraceptive vaccine formulation comprising an antigen as given above, in an amount effective to reduce the fertility of a subject, in combination with a pharmaceutically acceptable carrier.

A seventh aspect of the present invention is a method of screening for autoimmune infertility in a subject (e.g., a male subject), comprising detecting the presence of antibodies in the subject which bind to an antigen as given above, the presence of said antibodies indicating the subjected is afflicted with autoimmune infertility.

An eighth aspect of the present invention is an avirulent host cell (e.g., a microbial host cell) containing a recombinant DNA sequence encoding an antigen as given above and capable of expressing the encoded antigen.

A ninth aspect of the present invention is an immunocontraceptive vaccine formulation comprising an avirulent host cell as described above, in an amount effective to reduce the fertility of a subject, in combination with a pharmaceutically acceptable carrier.

In a preferred embodiment of the foregoing, the avirulent microbe lacks a functioning native chromosomal gene encoding β-aspartate semialdehyde dehydrogenase (asd), and further comprises a recombinant gene encoding a functional asd polypeptide. The recombinant gene is linked to one or more genes encoding one or more antigen as given above. The avirulent microbe may also include a mutated cya gene such that the microbe is substantially incapable of producing functional adenylate cyclase, and/or a mutated crp gene, rendering the microbe substantially incapable of producing functional cyclic AMP receptor protein.

The present invention is explained in greater detail in the drawings herein and the specification set forth hereinbelow.

Figure 1:
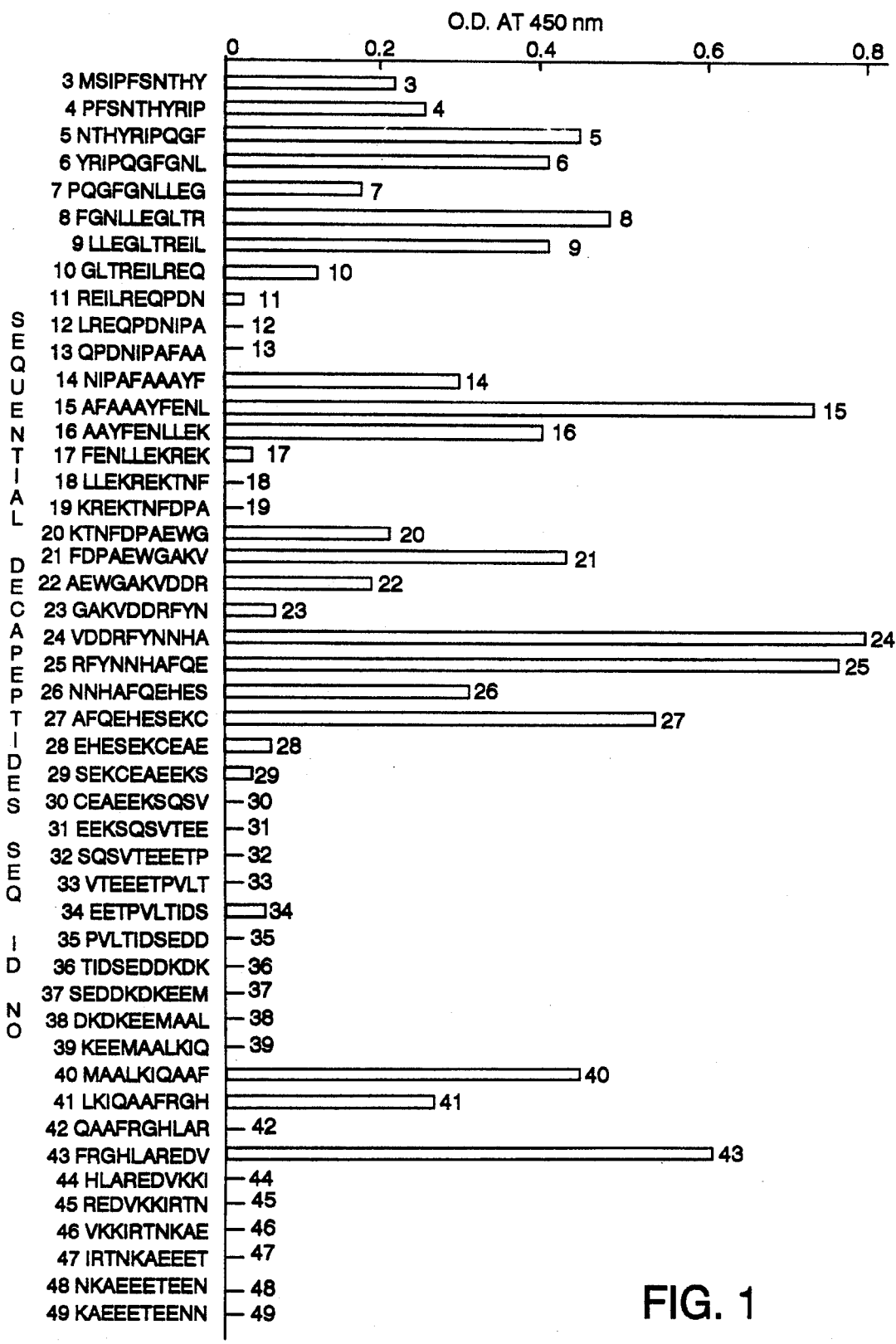
FIG. 1 shows the binding of antiserum from a male rabbit injected with his own sperm on binding to the rabbit Sp17 sequential decapeptides having the amino acid sequences disclosed herein as SEQ ID NO:3 through SEQ ID NO:49. In this figure, the SEQ ID NO for each decapeptide is given to the left and/or right thereof.
Figure 2:
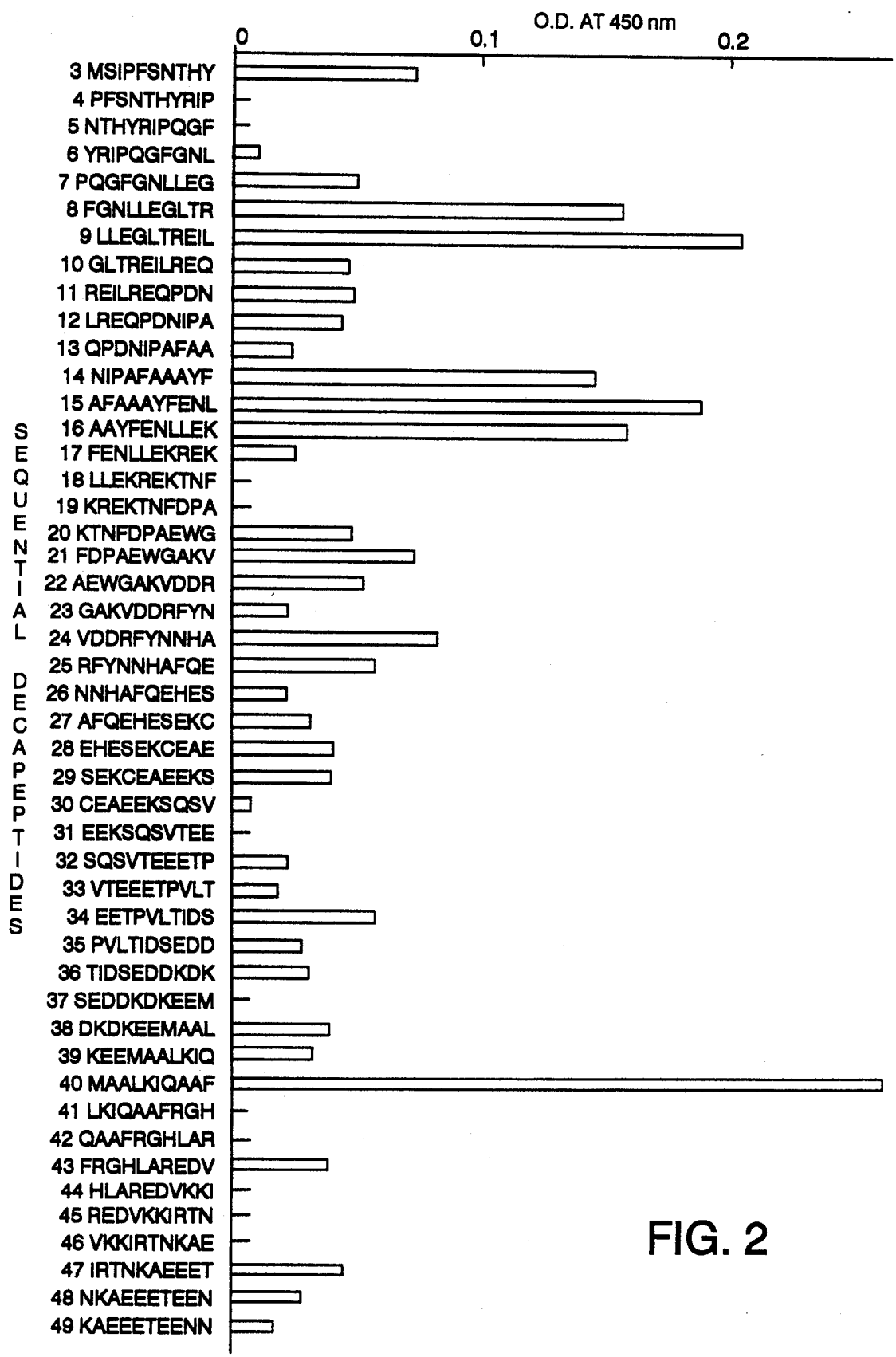

FIG. 2 shows the binding of a pool of sera from four vasectomized men with high titers of antisperm antibodies tested against the rabbit Sp17 sequential decapeptides used in FIG. 1. All the peaks on this graph represent human autoantigenic, B-cell epitopes.

Figure 3:
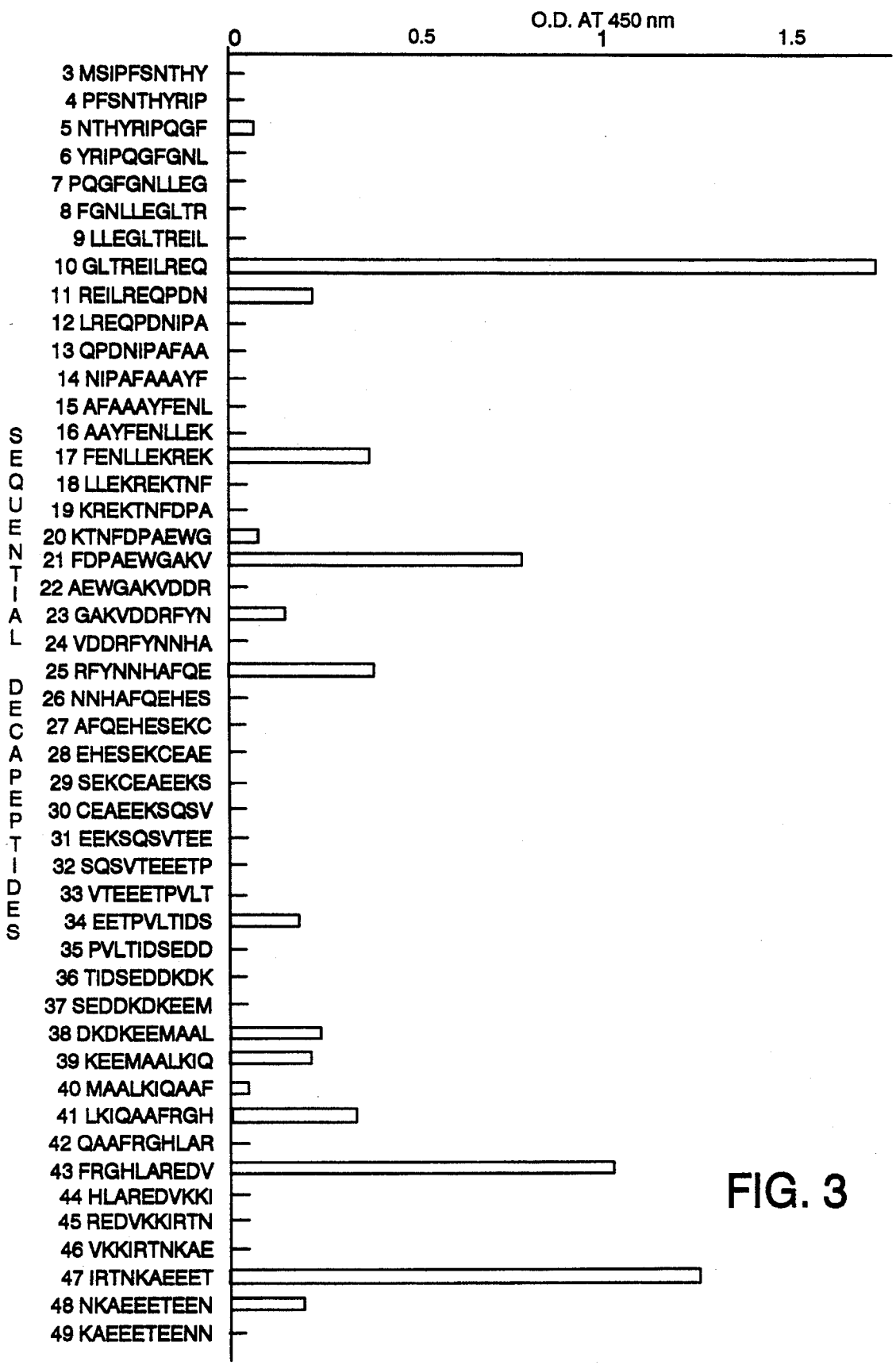

FIG. 3 shows the binding of immune sera from a female rabbit immunized with rabbit Sp17 recombinant antigen to the sequential decapeptides described in FIG. 1.

Figure 4:
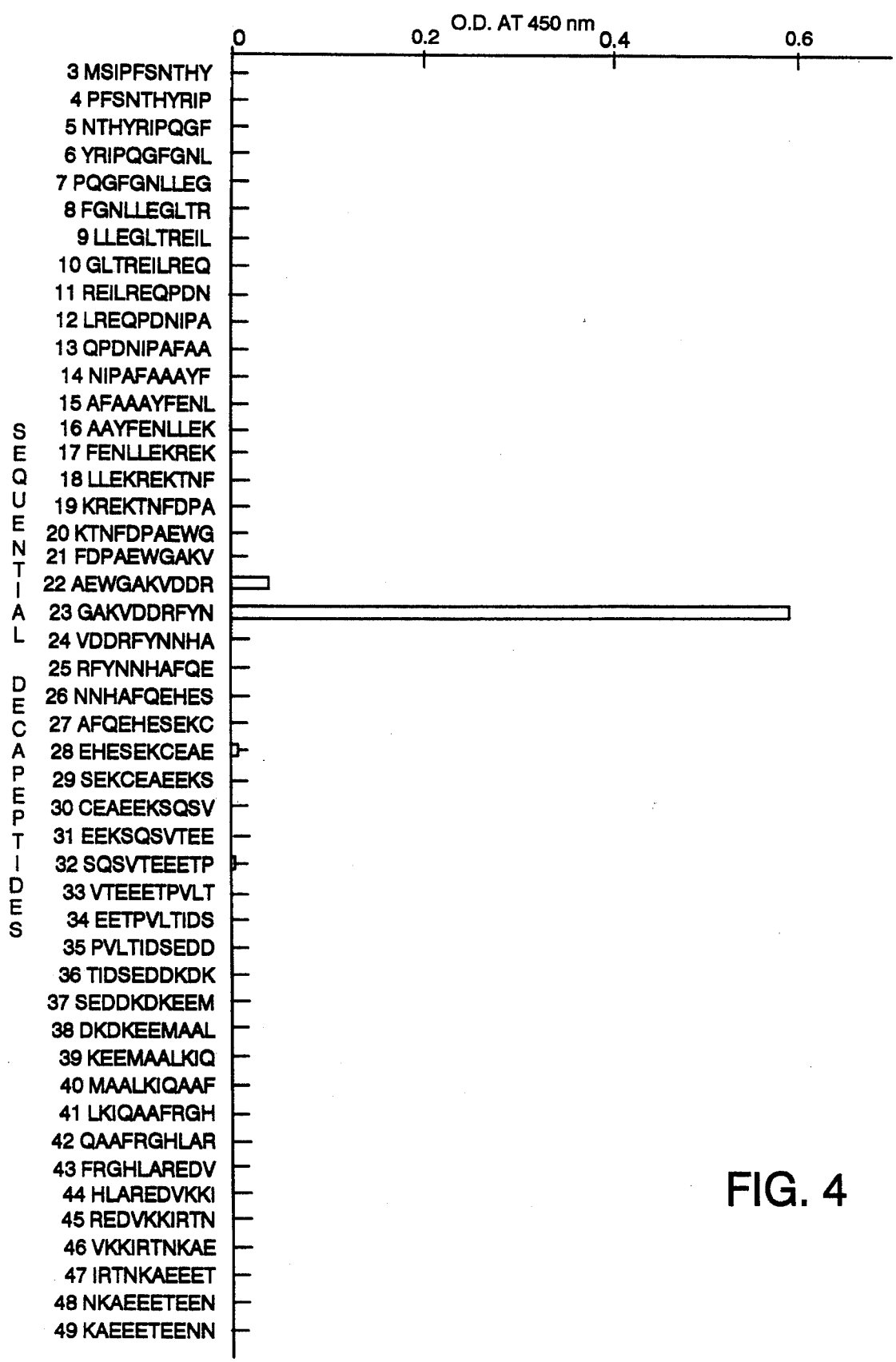

FIG. 4 shows the binding of immune sera taken from a male rabbit immunized with the synthetic peptide G22C to the sequential decapeptides described in FIG. 1.

Figure 5:
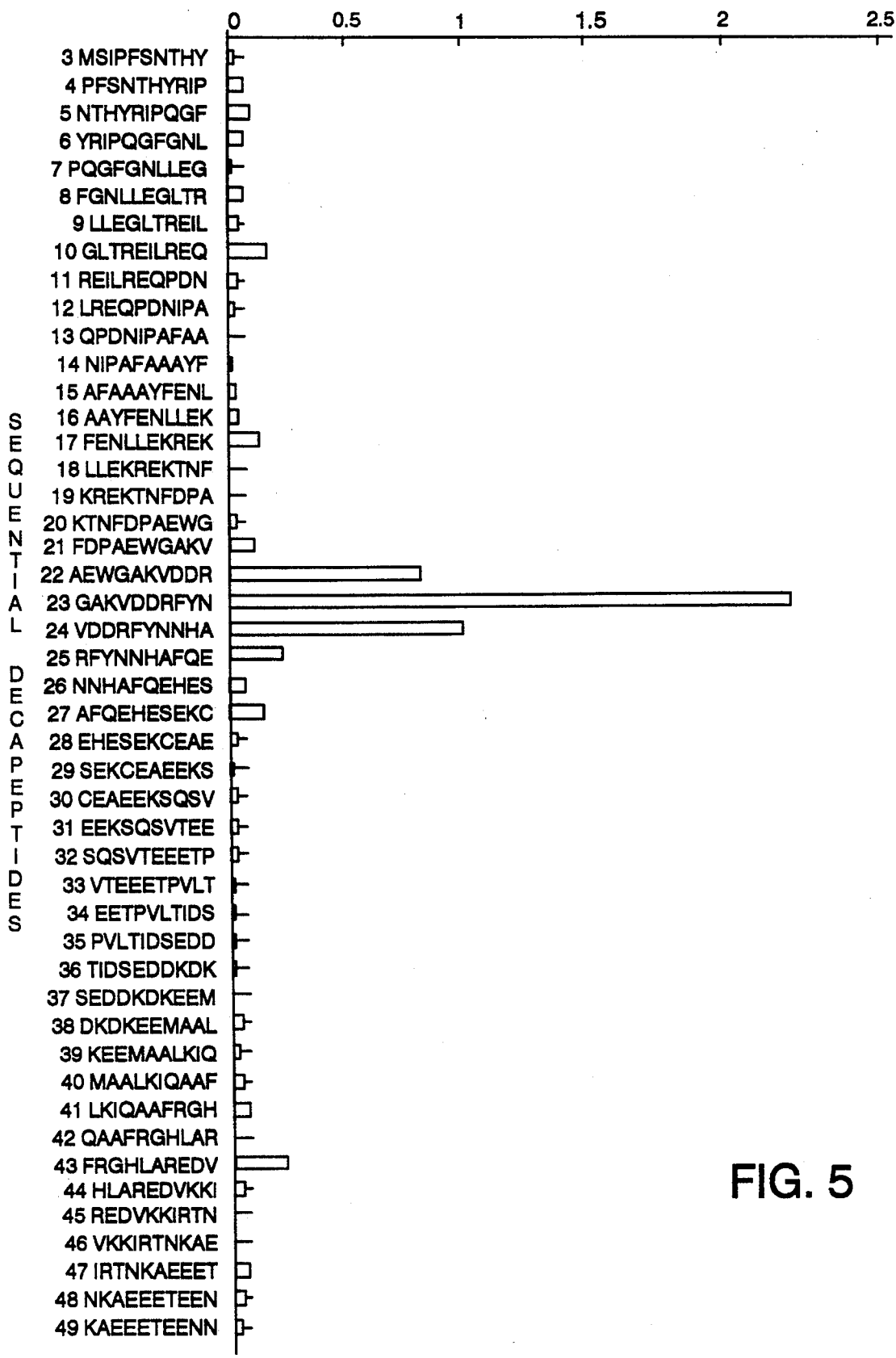

FIG. 5 shows the binding of immune sera taken from a female rabbit immunized with the synthetic peptide G22C to the sequential decapeptides described in FIG. 1.

Figure 6:
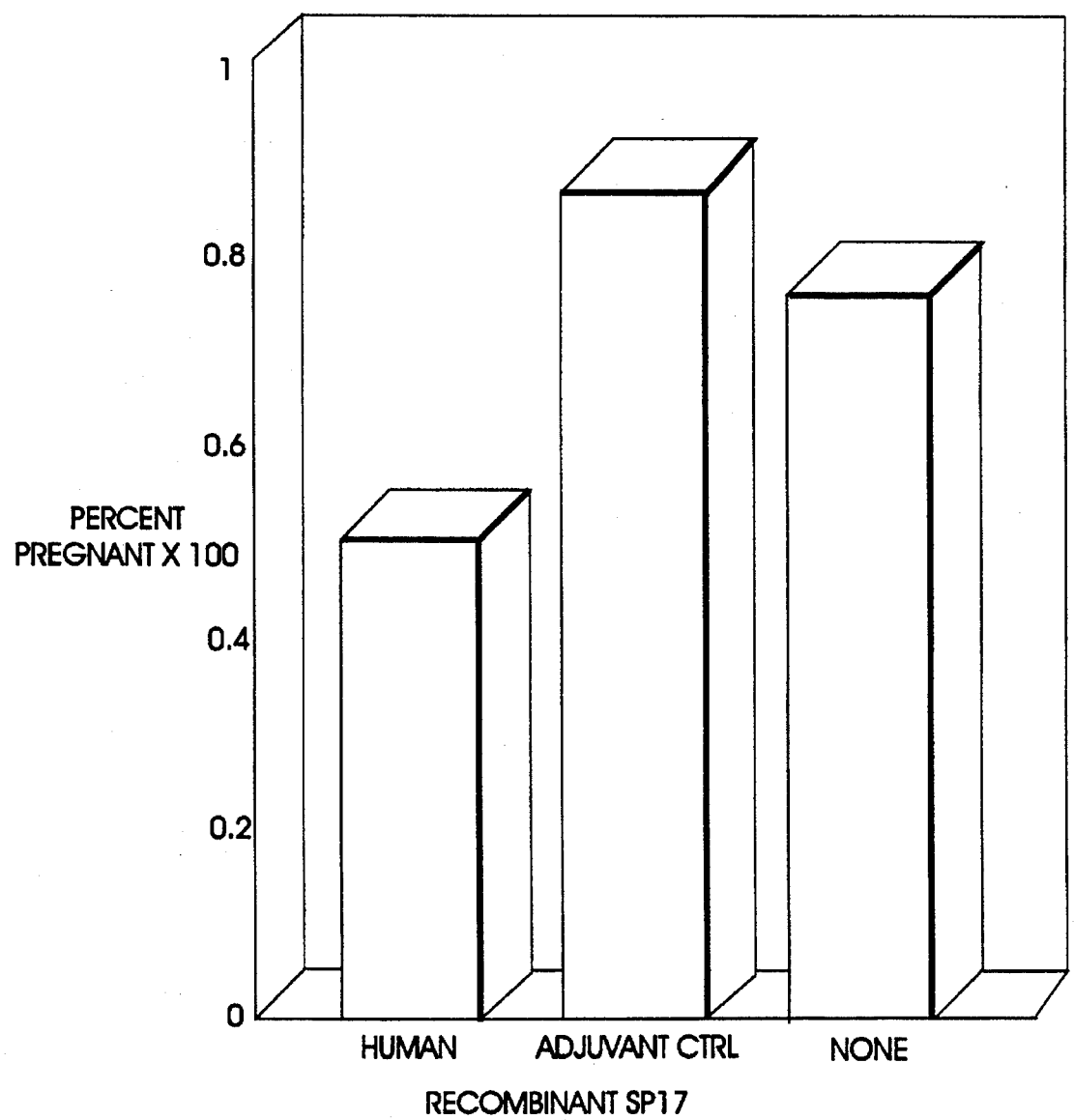

FIG. 6 illustrates the effect of immunization of mice with recombinant Sp17 (fusion protein) on fertility. Six mice received received human Sp17. Adjuvant controls (n=12) received TITERMAX™ adjuvant (available from Sigma Co., St. Louis) only. Six mice received no injections. The mice immunized with the human Sp17 recombinant protein showed a 42% decrease in pregnancy.

FIG. 7 gives the alignment of the rabbit (RABSP17), mouse (MUSSP17), and human (HUMSP17) Sp17 protein sequences. Autoantigenic fragments are indicated in the boxes. Numbering is from N-terminus to C-terminus, based on the numbering of the human sequence, with gaps introduced into the other mammalian sequences to maximize alignment of the autoantigenic fragments shown in the boxes, and numbers skipped where gaps are introduced so that the numbering of the autoantigenic fragments indicated in the boxes corresponds across species.

DETAILED DESCRIPTION OF THE INVENTION

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., Patent In User Manual, 99–102 (Nov. 1990)(U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend that the disclosure of this and all other patent references cited herein be incorporated herein by reference).

A. Molecular Biology

DNAs which encode human Sp 17 proteins, whether they are cDNAs or genomic DNAs, encode a protein of about 17 Kilodaltons which binds to human zona psilucida at high affinity by binding sulfated, complex carbohydrates. This definition is intended to encompass natural allelic variations in the DNAs.

DNAs encoding Sp 17 proteins which hybridize to the DNA encoding the human Sp 17 protein disclosed herein, may be of any species of origin, including murine (mouse, rat), rabbit, cat., porcine, human, monkey, or baboon, but preferably code for an Sp 17 protein of mammalian origin, and most preferably code for human Sp 17 proteins. Synthetic DNAs may be made in accordance with known techniques.

Hybridization conditions which will permit other DNA sequences which code on expression for an Sp 17 protein to hybridize to a DNA sequence as given herein are, in general, high stringency conditions. For example, hybridization of such sequences may be carried out under conditions represented by a wash stringency of 0.3 M NaCl, 0.03M sodium citrate, 0.1% SDS at 60° C. or even 70° C. to DNA disclosed herein (e.g., SEQ ID NO:1) in a standard in situ hybridization assay. (See J. Sambrook et al., Molecular Cloning, A Laboratory Manual (2d Ed. 1989)(Cold Spring Harbor Laboratory)).

In general, DNA sequences which code for Sp 17 proteins and hybridize to the DNA sequence encoding the human Sp 17 protein disclosed herein will be at least 70%, 75%, 80%, 85%, 90%, or even 95% homologous or more with the sequence of the DNA encoding the human Sp 17 protein disclosed herein.

In general, DNA sequences which encode human Sp 17 proteins which hybridize to the DNA encoding the human Sp 17 protein disclosed herein will be 93%, 94%, 95%, 96%, or even 97% homologous or more to the DNA sequence encoding the human Sp 17 protein disclosed herein.

Further, DNA sequences which code for the same Sp 17 protein as coded for by the foregoing sequences, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding Sp 17 proteins as given herein and/or to express DNA which encodes Sp 17 proteins as given herein. An expression vector is a replicable DNA construct in which a DNA sequence encoding a Sp 17 protein is operably linked to suitable control sequences capable of effecting the expression of the DNA sequence in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Typical vectors include, but are not limited to, plasmids, viruses, phage, and integratable DNA fragments (i.e., fragments integratable into the host genome by recombination).

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a DNA sequence as disclosed herein constructed using recombinant DNA techniques. Transformed host cells ordinarily express the receptor, but host cells transformed for purposes of cloning or amplifying the receptor DNA do not need to express the receptor.

Suitable host cells include prokaryote, yeast or higher eukaryotic cells such as mammalian cells and insect cells. Cells derived from multicellular organisms are a particularly suitable host for recombinant Sp 17 protein synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, and Chinese hamster ovary (CHO) cell lines. Expression vectors for such cells ordinarily include (if necessary) an origin of replication, a promoter located upstream from the DNA encoding the Sp 17 protein to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the receptor DNA. Examples of suitable selectable markers are dihydrofolate reductase (DHFR) or thymidine kinase. This method is further described in U.S. Pat. No. 4,399,216.

Host cells such as insect cells (e.g., cultured *Spodoptera frugiperda* cells) and expression vectors such as the baculovirus expression vector may be employed in carrying out the present invention, as described in U.S. Pat. Nos. 4,745, 051 and 4,879,236 to Smith et al.

Prokaryote host cells include gram negative or gram positive organisms, for example *Escherichia coli* (*E. coli*) or Bacilli.

Eukaryotic microbes such as yeast cultures may also be transformed with vectors carrying the isolated DNA's disclosed herein. see, e.g., U.S. Pat. No. 4,745,057. *Saccharomyces cerevisiae* is the most commonly used among lower eukaryotic host microorganisms., although a number of other strains are commonly available.

B. Peptides

One group of example antigenic fragments of the present invention, illustrated by FIG. 1 herein, are antigenic fragments selected from the group consisting of peptides having the amino acid sequence given herein as: SEQ ID NO:3, SEQ ID NO;4, SEQ ID NO:5, SEQ ID NO:6, SEQ ID NO:7, SEQ ID NO:8, SEQ ID NO:9, SEQ ID NO:10, SEQ ID NO:11, SEQ ID NO:14, SEQ ID NO:15, SEQ ID NO:16, SEQ ID NO:17, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:34, SEQ ID NO:40, SEQ ID NO:41, SEQ ID NO:43, and fragments thereof which are at least six amino acids in length. Of these, particularly preferred are antigenic fragments selected from the group consisting of peptides having the amino acid sequence given herein as: SEQ ID NO:5, SEQ ID NO:6, SEQ ID NO:8, SEQ ID NO:9, SEQ ID NO:14, SEQ ID NO:15, SEQ ID NO:16, SEQ ID NO:20, SEQ ID NO:21, SEQ ID NO:22, SEQ ID NO:24, SEQ ID NO:25, SEQ ID NO:26, SEQ ID NO:27, SEQ ID NO:40, SEQ ID NO:41, SEQ ID NO:43, and fragments thereof which are at least six amino acids in length.

Another group of example antigenic fragments of the present invention, illustrated by FIG. 2 herein, are antigenic fragments selected from the group consisting of peptides having the amino acid sequence given herein as: SEQ ID NO;3, SEQ ID NO;6, SEQ ID NO;7, SEQ ID NO;8, SEQ ID NO;9, SEQ ID NO;10, SEQ ID NO;11, SEQ ID NO;12, SEQ ID NO;13, SEQ ID NO;14, SEQ ID NO;15, SEQ ID NO;16, SEQ ID NO;17, SEQ ID N0;20, SEQ ID NO;21, SEQ ID NO;22, SEQ ID NO;23, SEQ ID N0;24, SEQ ID NO;25, SEQ ID NO;26, SEQ ID NO;27, SEQ ID N0;28, SEQ ID NO;29, SEQ ID NO;30, SEQ ID NO;32, SEQ ID NO;33, SEQ ID NO;34, SEQ ID NO;35, SEQ ID NO;36, SEQ ID NO;38, SEQ ID NO;39, SEQ ID NO;40, SEQ ID NO;43, SEQ ID NO;47, SEQ ID NO;48, SEQ ID NO;49, and fragments thereof which are at least six amino acids in length. Of these, particularly preferred are antigenic fragments selected from the group consisting of peptides having the amino acid sequence given herein as: SEQ ID NO;8, SEQ ID NO;9, SEQ ID NO;14, SEQ ID NO;15, SEQ ID NO;16, SEQ ID NO;21, SEQ ID NO;22, SEQ ID NO;24, SEQ ID NO;25, SEQ ID NO;34, SEQ ID NO;40, SEQ ID NO;43, and fragments thereof which are at least six amino acids in length.

In general, longer peptides preferably include the sequence of an antigenic peptide as described above. Longer peptides provide the antigenic sequence in an exposed position on the molecule, and not buried in the interior of the molecule where it would be unavailable for a binding event. Longer peptides which add not more than four additional amino acids to either the N terminal or C terminal of the antigen are preferred because sequences of such length are generally insufficient to provide an additional epitope on the longer peptide which might be detrimental to the activity of the antigen.

Peptides which may be used to carry out the present invention include analogs thereof. As used herein, analogs are those compounds which, while not having amino acid sequences identical to those of the peptides described above, have a similar three-dimensional structure. In protein molecules which interact with a receptor, the interaction between the protein and the receptor must take place at the surface-accessible sites in a stable three-dimensional molecule. By arranging the critical binding site residues in an appropriate conformation, peptides which mimic the essential surface features of the peptides of the present invention are designed and synthesized in accordance with known techniques. Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. patent references cited herein be incorporated by reference herein in their entirety). See also Waldrop, *Science*, 247, 28029 (1990); Rossmann, *Nature*, 333, 392–393 (1988); Weis et al., *Nature*, 333, 426–431 (1988). Techniques for constructing and screening libraries of peptide sequences to identify peptides that specifically bind to a given protein are known. Scott and Smith, *Science*, 249, 386–390 (1990); Devlin et al., *Science*, 249, 404–406 (1990). Further, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention.

In peptides containing substitutions or replacements of amino acids, one or more amino acids of a peptide sequence may be replaced by one or more other amino acids which does not affect the antigenicity of that sequence. Such changes can be guided by known similarities between amino acids in physical features such as charge density, hydrophobicity/hydrophilicity, size and configuration, so that amino acids are substituted with other amino acids having essentially the same functional properties. For example:

Ala may be replaced with Val or Ser;

Val may be replaced with Ala, Leu, Met, or Ile, preferably Ala or Leu;

Leu may be replaced with Ala, Val or Ile, preferably Val or Ile;

Gly may be replaced with Pro or Cys, preferably Pro;

Pro may be replaced with Gly, Cys, Ser, or Met, preferably Gly, Cys, or Ser;

Cys may be replaced with Gly, Pro, Ser, or Met, preferably Pro or Met;

Met may be replaced with Pro or Cys, preferably Cys;

His may be replaced with Phe or Gln, preferably Phe;

Phe may be replaced with His, Tyr, or Trp, preferably His or Tyr;

Tyr may be replaced with His, Phe or Trp, preferably Phe or Trp;

Trp may be replaced with Phe or Tyr, preferably Tyr;

Asn may be replaced with Gln or Ser, preferably Gln;

Gln may be replaced with His, Lys, Glu, Ash, or Ser, preferably Asn or Ser;

Ser may be replaced with Gln, Thr, Pro, Cys, or Ala;

Thr may be replaced with Gln or Ser, preferably Ser;

Lys may be replaced with Gln or Arg;

Arg may be replaced with Lys, Asp or Glu, preferably Lys or Asp;

Asp may be replaced with Lys, Arg, or Glu, preferably Arg or Glu; and

Glu may be replaced with Arg or Asp, preferably Asp.

Once made, changes can be routinely screened to determine their effects on antigenicity with antibodies which bind to the antigen.

The term "antigenic equivalents" as used herein, refers to proteins or peptides which bind to an antibody which binds to the protein or peptide with which equivalency is sought to be established. Antibodies which are used to select such antigenic equivalents are referred to as "selection antibodies" herein. Antigenic equivalents may be formed by modifying reactive groups within a natural sequence or modifying the N-terminal animo and/or C-terminal carboxyl group. Such equivalents include salts formed with acids and/or bases, particularly physiologically acceptable inorganic and organic acids and bases. Other equivalents include modified carboxyl and/or amino groups on the antigen to produce esters or amides, or amino acid protecting groups such a N-t-butoxycarbonyl. Preferred modifications are those which provide a more stable, active peptide which will be less prone to enzymatic degradation in vivo.

C. Immunocontraceptive Methods

As noted above, the present invention provides an immunocontraceptive method comprising administering an animal subject an antigen as described above in an amount effective to reduce the fertility of that subject. Partial reductions in fertility (i.e., effects which are reflected as a reduction in fertility in a population of subjects) are intended as within the scope of the present invention.

Any animal may be treated by the immunocontraceptive method of the present invention, including both birds and mammals. Exemplary mammals include mice, rabbits, dogs, cats, cows, pigs, sheep, horses and humans. Mammalian subjects are preferred. The subject may be male or female. The antigen may be administered to the subject by any suitable means. Exemplary are by intramuscular injection, by subcutaneous injection, by intravenous injection, by intraperitoneal injection, by oral administration, and by nasal spray.

The amount of antigen administered will depend upon factors such as route of administration, species, and the use of booster administrations. In general, a dosage of about 0.1 to about 100 µg per pound subject body weight may be used, more particularly about 1 µg per pound.

The immunocontraceptive method of the present invention contemplating both human and veterinary treatments, the antigens of the present invention may be prepared as both human and veterinary vaccine formulations. Vaccine formulations of the present invention comprise the antigen in a pharmaceutically acceptable carrier. The antigen is included in the carrier in an amount effective to reduce the fertility of the subject being treated. Pharmaceutically acceptable carriers are preferably liquid, particularly aqueous, carriers, such as sodium phosphate buffered saline. The vaccine formulation may be stored in a sterile glass container sealed with a rubber stopper through which liquids may be injected and formulations withdrawn by syringe.

Vaccine formulations of the present invention may optionally contain one or more adjuvants. Any suitable adjuvant can be used, exemplary being aluminum hydroxide, aluminium phosphate, plant and animal oils, and the like, with the amount of adjuvant depending on the nature of the particular adjuvant employed. In addition, the vaccine formulations may also contain one or more stabilizer, exemplary being carbohydrates such as sorbitol, mannitol, starch, sucrose, dextrin, and glucose, proteins such as albumin or casein, and buffers such as alkaline metal phosphate and the like.

D. Diagnostic Methods

The diagnostic methods of the present invention provide a method of diagnosing autoimmune infertility in both male and female subjects. The term "autoimmune" is here used in a generic sense, as the immunity in female subjects is to exogenous sperm.

Any conventional procedure for detecting antibodies can be employed in practicing the diagnostic assay of the present invention, including agglutination and precipitation reactions, radioimmunoassays, enzyme immunoassays (e.g., U.S. Pat. No. 3,654,090) such as Enzyme-Linked Immunosorbent Assays (ELISA), heterogeneous fluorescent immunoassays (e.g., U.S. Pat. Nos. 4,201,763; 4,171,311; and 3,992,631), and homogeneous (separation-free) immunoassays. See generally *Basic and Clinical Immunology*, 364–73 (J. Fudenberg et al., eds. 3d Ed. 1980), ELISA is preferred.

In a preferred embodiment, serum from a human to be diagnosed is contacted with an antigen as described above so that antibodies in the serum react in solution with the antigen. While the antigen is preferably bound to a solid support, if a homogeneous (separation free) immunoassay is utilized to detect the antibodies, a solid support would not be required.

Serum may be obtained from a person generally pricking a finger and obtaining whole blood (of which serum is a constituent). However, the blood may be processed to obtain only the serum or plasma portion of the whole blood before contacting the serum with the bound antigens. Any method for obtaining serum or plasma from a patient may be utilized as long as the antibodies contained therein retain their ability to bind the antigen.

The antigens may be bound to solid supports by known techniques. For example, a bi-functional organic molecule may be used to attach the antigen to a solid support. The solid can be made of materials such as plastic (e.g., the bottom surface of a well in a microtiter plate), fiberglass, cellulose acetate and nitrocellulose (e.g., discs). After being attached or adhered to the solid support, the antigens can be cross-linked if desired.

The step of contacting the solid support with a detectable antibody is carried out so that the detectable antibody is allowed to interact with the antigen bound to the solid support. The detectable antibody is one which is capable of binding to a human antibody from the serum of the patient which has bound to the purified antigen, where the detectable antibody is capable of being detected. More particularly, the detectable antibody can be an anti-human immunoglobulin which is conjugated to a group such as an enzyme which is detectable in the presence of a substrate. Enzyme-conjugated goat or rabbit anti-human antibodies which have been affinity purified are preferred. In general, the detectable group which is conjugated to the detectable antibody may be any enzyme or other detectable species which has been developed for immunoassays. For example, enzymes, fluorescent groups, radioactive groups and others could be used. The enzyme peroxidase is particularly preferred. When peroxidase is the detectable group conjugated to the detectable antibody, a substrate such as 3.3', 5.5'-tetramethylbenzidine or o-phenylenediamine may be used as the substrate for detection of the detectable antibody.

The step of detecting the detectable antibody that has reacted with the human antibodies involves treating or manipulating the detectable group which is conjugated to the detectable antibody to determine its presence. For example, if an enzyme such as peroxidase is conjugated to the antibody, the detecting step would involve adding a peroxidase substrate to the bound antibody, and adding a peroxidase substrate to the bound antibody and observing a color change as peroxidase catalyzes conversion of the substrate to a colored species. In the case of other enzymes, such as alkaline phosphatase and β-D-galactosidase, other substrates may be used. The substrate to be used should be chosen such that after the enzyme catalyzes a chemical conversion of the substrate to a product, a change which is observable to a person employing this test should result. Substrates such as 3.3', 5.5'-terramethylbenzidine, p-nitrophenyl phosphate or 3.3'-diamino-benzidine may be used as substrates. Other detectable groups may also be conjugated to the antibody.

A kit containing the required components for carrying out a diagnostic test based on detection of serum antibodies can be assembled. The kit comprises a package containing purified antigen coated in or on a solid support such as the bottom of a microtiter plate well or a nitrocellulose or cellulose acetate disc, and a container of a detectable antibody conjugate which is capable of binding antibody from the serum of a patient which is bound to the antigen. An ELISA test is most preferred for the kit since it lends itself to a readily detectable positive or negative diagnosis. Thus, the kit should also house a container of a substrate which is reactive with an enzyme which is conjugated to the detectable antibody, the substrate being readily detectable after reaction with the enzyme. The antigen employed in the diagnostic kit is preferably substantially or essentially free of other proteins.

E. Avirulent Carrier Cells

As noted above, avirulent carrier cells such as microbes are used to administer antigens of the present invention. This method is particularly suitable since appropriate carrier microbes can stimulate production of sIgA to the antigens which they express. Suitable avirulent carrier cells, including both plant carrier cells and microbial carrier cells, are described in R. Curtiss, Vaccines Obtained from Antigenic Gene Products of Recombinant Genes, U.S. Pat. No. 4,888, 170, R. Curtiss and G. Cardineau, Oral Immunization by Transgenic Plants, PCT Application WO 90/02484, and R. Curtiss, Recombinant Avirulent Salmonella Antifertility Vaccines, PCT Application WO 92/09684, the disclosures of which are incorporated herein by reference.

In general, recombinant plasmids containing one or more genes for the gamete-specific antigens can be introduced into one of several avirulent strains of bacteria containing mutations for genes necessary for long-term survival in the targeted host. Useful avirulent microbes include, but are not limited to, mutant derivatives of Salmonella and *E. coli-Salmonella* hybrids. Preferred microbes are members of the genus Salmonella such as *S. typhimurium*, *S. typhi*, *S. parathyphi*, *S. gallinarum*, *S. pullorum*, *S. enteritidis*, *S. choleraesuis*, *S. arizona*, or *S. dublin*. Avirulent derivatives of *S. typhimurium* and *S. enteritidis* find broad use among many hosts. Avirulent derivatives of *S. gallinarum*, *S. pullorum* and *S. arizona* may be particularly useful for immunizing avian species whereas *S. typhimurium*, *S. typhi* and *S. parathyphi* are preferred for use in humans. *S. choleraesuis* is preferably used to immunize swine while *S. dublin* finds use in cattle.

Particularly useful are one, two or all three of the cya, crp and asd mutants which are substantially incapable of producing the corresponding functional protein in a host, such that growth is impaired. However, other avirulent microbes will also find use with the present invention. Such avirulent microbes include those with aroA, aroD, galE, phoP, cdt, omoR and htrA mutations. If Asd mutants are used, the antigen of interest is transferred to the carrier microbe using a vector encoding both the antigen and asd. Thus, only those carrier microbes containing the desired gamete-specific antigen will survive and these microbes can be selected for further use. Expression of the recombinant gene encoding the desired antigen maybe dependent on a control sequence linked to the asdgene. This linkage may result from the orientation of the two genes in the vector so that both genes could be, for example, under the control of the same control elements, i.e., the same promoter and operator.

The cyp mutants and/or crp mutants can be further mutated, preferably by a deletion, in a gene adjacent to the crp gene which governs virulence of Salmonella. Mutation in this gene, the cdt gene, diminishes the ability of the bacteria to effectively colonize deep tissues, e.g., the spleen. When a plasmid having the $crp^+$ gene is placed in a strain with the Δ(crp-cdt), it retains its avirulence and immunogenicity thus having a phenotype similar to cya and crp mutants. Mutants with the A(crp-cdt) mutation containing a $crp^+$ gene on a plasmid retain the normal ability to colonize the intestinal tract and GALT, but have a diminished ability to colonize deeper tissues.

In order to stimulate a preferred immune response, introduction of the microbe or gene product directly into the gut or bronchus is preferred, such as by oral administration, intranasal administration, gastric intubation or in the form of aerosols, as well as air sac inoculation (in birds only), and intratracheal inoculation. Other suitable methods include administration via the conjunctiva to reach the Harder gland and intramammary inoculation. Other methods of administering the vaccine, such as intravenous, intramuscular, or subcutaneous injection are also possible, and used principally to stimulate a secondary immune response, as described further below.

Generally, when carrier microbes expressing the antigens are administered to humans or other mammals, they will be present in a pharmaceutically acceptable carrier. For example, the carrier microbes can be enteric-coated or encapsulated with a suitable gelatin-like substance, known in the art (Cryz and Glück, 1990, in G. Woodrow and Mr. Levine, New Generation Vaccines, Marcel Dekker, New York, pp. 921–932).

Once the carrier microbe is present in the animal, the antigen must become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell.

The antigens may also be administered as aerosols or intranasally. Intranasal formulations for human subjects will usually include vehicles that neither cause irritation to the nasal mucosa nor significantly disturb ciliary function. Diluents such as water, aqueous saline or other known substances can be employed with the subject invention. The nasal formulations may also contain preservatives such as but not limited to chlorobutanol and benzalkonium chloride. A surfactant may be present to enhance absorption of the subject proteins by the nasal mucosa.

Injection of the gamete-specific antigen can also be done in conjunction with prior oral, intranasal, gastric or aerosol immunization. Such parenteral immunization can serve as a booster to enhance expression of the secretory immune response once the secretory immune system to the gamete-specific gene product has been primed by immunization with the carrier microbe expressing the gamete-specific gene product. The enhanced response is known as a secondary, booster, or anamnestic response and results in prolonged immune protection of the host. Booster immunizations may be repeated numerous times with beneficial results.

When the vaccines are prepared as injectables, such as for boosters, they can be made either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th ed., 1975. The composition or formulation to be administered will, in any event, contain a quantity of the protein adequate to achieve the desired immunized state in the individual being treated.

The quantity of antigen to be administered depends on the subject to be treated, the capacity of the subject's immune system to synthesize antibodies, and the degree of protection desired. Effective dosages can be readily established by one of ordinary skill in the art through routine trials establishing dose response curves. The subject is immunized by administration of the particular antigen or fragment thereof, or analog thereof, in at least one dose. Typical doses using the carrier microbe are on the order of $1\times10^6$–$1\times10^{10}$ recombinant avirulent bacteria/immunized subject. The subject may be administered increasing amounts or multiple dosages as required to maintain a state of immunity to the gamete-specific antigen.

It may be desirable to administer more than one antigen simultaneously or consecutively. This can be accomplished either by administering an avirulent carrier containing genes encoding for more than one gamete-specific antigen or by administering different carrier organisms.

The present invention is explained below in the following non-limiting Examples.

EXAMPLE 1

Cloning and Sequencing of Human Sperm Zona Binding Protein Sp17

We have previously reported cloning and sequence data of rabbit Sp17 (Richardson and O'Rand, Mol. Biol. Cell 3, 15a (1992)). This protein is known to be a member of the rabbit sperm antigen (RSA) family of rabbit testis/spermautoantigens and also to be expressed in mice. Further search for a human counterpart of this protein was initiated with screening of a human testis cDNA library using the protein coding region of the rabbit Sp17 gens as a probe. One clone contained a 1287 base pair insert 71% identical to the rabbit Sp17 gene at the nucleotide level, contained an open reading frame of 455 base pairs, and had the sequence given herein as SEQ ID NO:1. This clone encoded a protein of 151 amino acids having the sequence given herein as SEQ ID NO:2 with a calculated molecular weight of 17,534 Da, 76.7% identical to the rabbit Sp17 and 71.8% identical to the mouse Sp17 protein sequence. In particular, the first 44 amino acids are completely identical in the mouse, rabbit and human sequences and have a 43% identity to the human testis cAMP dependent protein kinase type IIα regulatory sub-unit dimer interaction site. Interestingly, comparison of rabbit, mouse and human amino acid sequences has shown that the human Sp17 lacks the single cysteine residue at the center of the molecule which the other sequences possess. Northern blot analysis of a range of mouse, baboon and human tissues revealed a highly restricted pattern of gene expression limited to the testis. Additionally, Northern analysis has revealed evidence of 2 distinct transcript sizes of approximately 1.3 kb and 0.9 kb in the human testis. Antisera to Sp17 recombinant protein (rSp17) has been generated and used on Western blots of human sperm lysates to demonstrate a predominant immunoreactive protein of 29 KDa. The antigen was localized by immunofluorescence on human spermatozoa with anti-rSp17. In ELISA rSp17 was shown to bind fucoidan with saturation kinetics. Sera from vasectomized men who have anti-sperm antibody titres also shown reactivity to rSp17, indicating that human Sp17 is a human sperm autoantigen.

EXAMPLE 2

Production of Sequential Decapeptides and Immunoassay Procedures

A series of forty-seven N-terminal acetylated sequential decapeptides corresponding to fragments of the rabbit Sp17 protein were synthesized in accordance with known techniques; these decapeptides are disclosed herein as SEQ ID NO:3 through SEQ ID NO:49.

Enzyme-linked immunosorbent assay (ELISA) was carried out in accordance with known procedures (see, e.g., M. O'Rand et. al. Dev. Biol. 129, 231 (1988)), as adapted for the MULTIPIN™ system, in accordance with the manufacturer's specifications. (Chiron Mimotopes Pty. Ltd., Clayton, Victoria, 3168 Australia). Control O.D. values of IgG from a normal control subject were subtracted from experimental values in displaying the ELISA data below, in accordance with standard techniques.

EXAMPLE 3

Production of Antibodies to Peptide G22C

The peptide G22C, which corresponds to the fragment of rabbit Sp17 spanning amino acid 61 to amino acid 82 (and having the sequence: GAKVDDRFYNNHAFQEHESEKC) was synthesized at the Salk Institute under contract NO1-HD- 0-2906 with the NIH in accordance with standard techniques.

Male and female rabbits were immunized with G22C peptide which was conjugated to keyhole limpet hemocyanin (KLH) with the C-terminal Cys amino acid of G22C. Conjugation was carried out with Ellman's reagent, 5,5'-dithio-bis-[ 2-nitrobenzoic acid] obtained from Pierce Scientific in the form of the IMJECT® immunogen conjugation kit. Each rabbit received subcutaneous injection of 300 μg of conjugate in complete Freund's adjuvant followed by an additional 200 μg of conjugate in incomplete Freund's adjuvant three weeks later and a final 100 μg of conjugate in incomplete Freund's adjuvant three weeks later. Conjugate was provided in 100 μl of water diluted 1:1 with adjuvant.

EXAMPLE 4

Binding of Rabbit AutoImmune Sera to Rabbit Sp17 Sequential Decapeptides

A male rabbit was injected with his own sperm to produce autoimmune sera. Specifically, 2 mg of sperm was washed three times in PBS, resuspended in 0.5 ml of PBS, diluted 1:1 by volume with Freund's complete adjuvant, and injected subcutaneously. A first booster shot was given one month thereafter, a second booster was given an additional two weeks thereafter, a third booster was given an additional two weeks thereafter, and a fourth booster was given an additional three months thereafter. The immune sera was screened by ELISA as described above with the sequential decapeptides described above. Results are shown in FIG. 1. Note the clustering of potential autoantigenic epitopes.

EXAMPLE 5

Binding of Pooled Human AutoImmune Sera to Rabbit Sp17 Sequential Decapeptides FIG. 2 shows the binding of a pool of equal volumes of sera from four vasectomized men with high titers of anti-sperm antibodies tested against the sequential decapeptides described above by ELISA as described above. Note that all the peaks on FIG. 2 represent human autoantigenic B-cell epitopes.

EXAMPLE 6

Binding of Sp17-Immunized Rabbit Sera to Rabbit Sp17 Sequential Decapeptides The binding of immune sera from a female rabbit immunized with recombinant rabbit Sp17 fusion protein to the sequential decapeptides described above is shown in FIG. 3.

The recombinant fusion protein was generated by PCR using the following primers: for the plus strand, 5' -CGCGGATCCATGTCGATTCCATTTTCC-3' which contains a Bam HI site, and for the antisense primer, 5'-CGGGGTACCGCCAGTGCCCTCAATTGT- 3' which contains a Kpn I site. The PCR product was directionally cloned into the polylinker region of pQE- 30, sequenced to verify integrity of the insert, and bacterially expressed according to the protocol provided by Qiagen Inc. (Chatsworth, Calif.). Using this system, the recombinant rabbit Sp17 protein (rSp17) is expressed minus the first 11 N-terminal amino acids missing but with an N-terminal containing the Sequence Arg-Gly-Ser, followed by six histidines and a glycine which preced the Sp17 amino acids. The fusion protein was purified from the bacterial lysate by affinity chromatography using the metal chelate adsorbent nickel-NTA-agarose (Qiagen, Inc.). The fusion protein was eluted with 8M urea, 0.1M sodium phosphate (monobasic), 0.01M Tris, pH adjusted to 5.9, and dialyzed against three changes of PBS. 200 μg of protein in 0.5 ml PBS with 1 mg ADJUPRIME™ adjuvant (Pierce Chemical Co., Rockford, Ill., USA) was administered subcutaneously. A first booster of 200 μg in the same volume was given three weeks thereafter.

EXAMPLE 7

Binding of G22C-Immunized Rabbit Sera to Rabbit Sp17 Sequential Decapeptides The binding of immune sera taken from a male rabbit immunized with the synthetic peptide G22C as described in Example 3 above to the sequential decapeptides described above by ELISA as described above is shown in FIG. 4, and the binding of immune sera taken from a female rabbit immunized with the synthetic peptide G22C as described in Example 3 above to the sequential decapeptides described above is shown in FIG. 5.

EXAMPLE 8

Effect of Immunization of Mice with Recombinant Human Sp17 on Fertility

FIG. 6 illustrates the effect of immunization of mice with recombinant human Sp17 (fusion protein) on fertility. Six mice received only mouse Sp17, six received mouse and then rabbit Sp17, six received only human Sp17. Adjuvant controls (n=12) received TITERMAX™ adjuvant (available from Sigma Co., St. Louis) only. Six mice received no injections. The mice immunized with the human Sp17 recombinant protein showed a 42% decrease in pregnancy.

Recombinant human Sp17 was prepared as a fusion protein in essentially the same manner as described above for recombinant rabbit Sp17, except that no N-terminal Sp17 amino acids were deleted from the resulting product. Balb/c mice were immunized with approximately 5 μg of fusion protein in water diluted 1:1 with Freund's complete adjuvant. Four weeks after the first immunization, three more injections of the fusion protein in incomplete adjuvant were given every two weeks.

EXAMPLE 9

Alignment of Mammalian Sp17s

FIG. 7 gives the alignment of the rabbit (RABSP17), mouse (MUSSP17), and human (HUMSP17) Sp17 protein sequences. Autoantigenic fragments are indicated in the boxes. Numbering is from N-terminus to C-terminus, based on the numbering of the human sequence, with gaps introduced into the other mammalian sequences to maximize alignment of the autoantigenic fragments shown in the boxes, and numbers skipped where gaps are introduced so that the numbering of the autoantigenic fragments indicated in the boxes corresponds across species.

EXAMPLE 10

Binding of Recombinant Sp17 to Human Zona Pellucida

Biotinylated human recombinant Sp17 was shown to bind to human zona psilucida by ELISA. This is the first demonstration of binding of any recombinant mammalian Sp17 to any mammalian zona pellucida.

The foregoing examples are illustrative of the present invention, and are not to be construed as limiting thereof. The invention is defined by the following claims, with equivalents of the claims to be included therein.

---

That which is claimed is:

1. Isolated DNA encoding an Sp 17 protein selected from the group consisting of:
   (a) isolated DNA having the nucleotide sequence given herein as SEQ ID NO:1 which encodes the human Sp 17 protein having the amino acid sequence given herein as SEQ ID NO:2;
   (b) isolated DNA which hybridizes to isolated DNA of (a) above under conditions represented by a wash stringency of 0.3M NaCl, 0.03M sodium citrate, and 0.1% SDS at 60° C., and which encodes a human Sp 17 protein; and
   (c) isolated DNA differing from the isolated DNAs of (a) and (b) above in nucleotide sequence due to the degeneracy of the genetic code, and which encodes a human Sp 17 protein.

2. Isolated DNA according to claim 1 which encodes the human Sp 17 protein given herein as SEQ ID NO:2.

3. Isolated DNA according to claim 1 having the sequence given herein as SEQ ID NO: 1.

4. A recombinant DNA sequence comprising vector DNA and a DNA according to claim 1.

5. A host cell containing a recombinant DNA sequence of claim 4 and capable of expressing the encoded protein or peptide.

* * * * *